United States Patent [19]

Young et al.

[11] Patent Number: 4,744,368

[45] Date of Patent: May 17, 1988

[54] METHOD AND MEANS FOR DETECTING PREGNANCY IN DOMESTIC FARM ANIMAL

[75] Inventors: Donald F. Young; Leroy R. Waite; Stephen P. Ford; Alan J. Conley, all of Ames, Iowa

[73] Assignee: Iowa State University Research Foundation, Inc., Ames, Iowa

[21] Appl. No.: 862,711

[22] Filed: May 13, 1986

[51] Int. Cl.$^4$ .............................................. A61B 10/00
[52] U.S. Cl. ................................................. 128/663
[58] Field of Search ............................ 128/660–663, 128/4, 672, 687; 73/861.25

[56] References Cited

U.S. PATENT DOCUMENTS

| | | | |
|---|---|---|---|
| 2,755,796 | 7/1956 | Bouche | 128/687 |
| 4,144,877 | 3/1979 | Frei et al. | 128/774 |
| 4,237,729 | 12/1980 | McLeod . | |
| 4,314,563 | 2/1982 | Wheeler . | |
| 4,336,808 | 6/1982 | Ohno et al. . | |
| 4,355,643 | 10/1982 | Laughlin et al. | 128/663 |
| 4,416,286 | 11/1982 | Iinuma et al. . | |
| 4,434,669 | 3/1984 | Roberts et al. . | |
| 4,476,874 | 10/1984 | Toenzer et al. | 128/663 |
| 4,545,386 | 10/1985 | Hetz et al. | 128/660 |
| 4,582,066 | 4/1986 | Barnes et al. | 128/661 |
| 4,674,517 | 6/1987 | Barnes et al. | 128/663 |

OTHER PUBLICATIONS

Janbu, T. et al, "Blood Velocities in the Uterine Artery in Humans during Labor", Acta Physiol—Scand. 1985, V. 24 pp. 153–161.
Campbell, S. et al "New Doppler Technique For Assessing Uteroplacental Blood Flow", Lancet vol. 1 (1983) pp. 675–677.
Olson, R. M. et al., "Human Carotid Artery Diameter and Flow by a Non–Invasive Technique", Medical Instrumentation vol. 9 No. 2 Mar.-Apr. 1975 pp. 99–102.

Primary Examiner—Francis J. Jaworski
Attorney, Agent, or Firm—Zarley McKee, Thomte, Voorhees & Sease

[57] ABSTRACT

A device for detecting pregnancy in animals comprises a finger receptacle adapted to fit over a human finger. On the outer surface of the receptacle is a transducer housing having a transducer therein for transmitting ultrasonic sound waves and for receiving echo ultrasonic sound waves in response thereto and converting the echo ultrasonic sound waves into an electrical echo signal. Electrical leads carry the echo signal from the transducer to a computer or a strip chart recorder for analyzing and visually displaying indices which provide an indication of the velocity of the blood flow detected in the uterine artery of the animal by the transducer.

The method of the present invention comprises placing the transducer in contact with the uterine artery of the animal, and measuring the velocity of blood flow in the uterine artery. An increase in the blood flow over the animal's normal blood flow in the uterine artery is an indication of pregnancy. The blood flow of the uterine artery in one horn of the animal's uterus can be compared to the blood flow of the uterine artery in the other horn of the animal's uterus to determine whether one of the two uterine horns has a developing embryo therein.

4 Claims, 3 Drawing Sheets

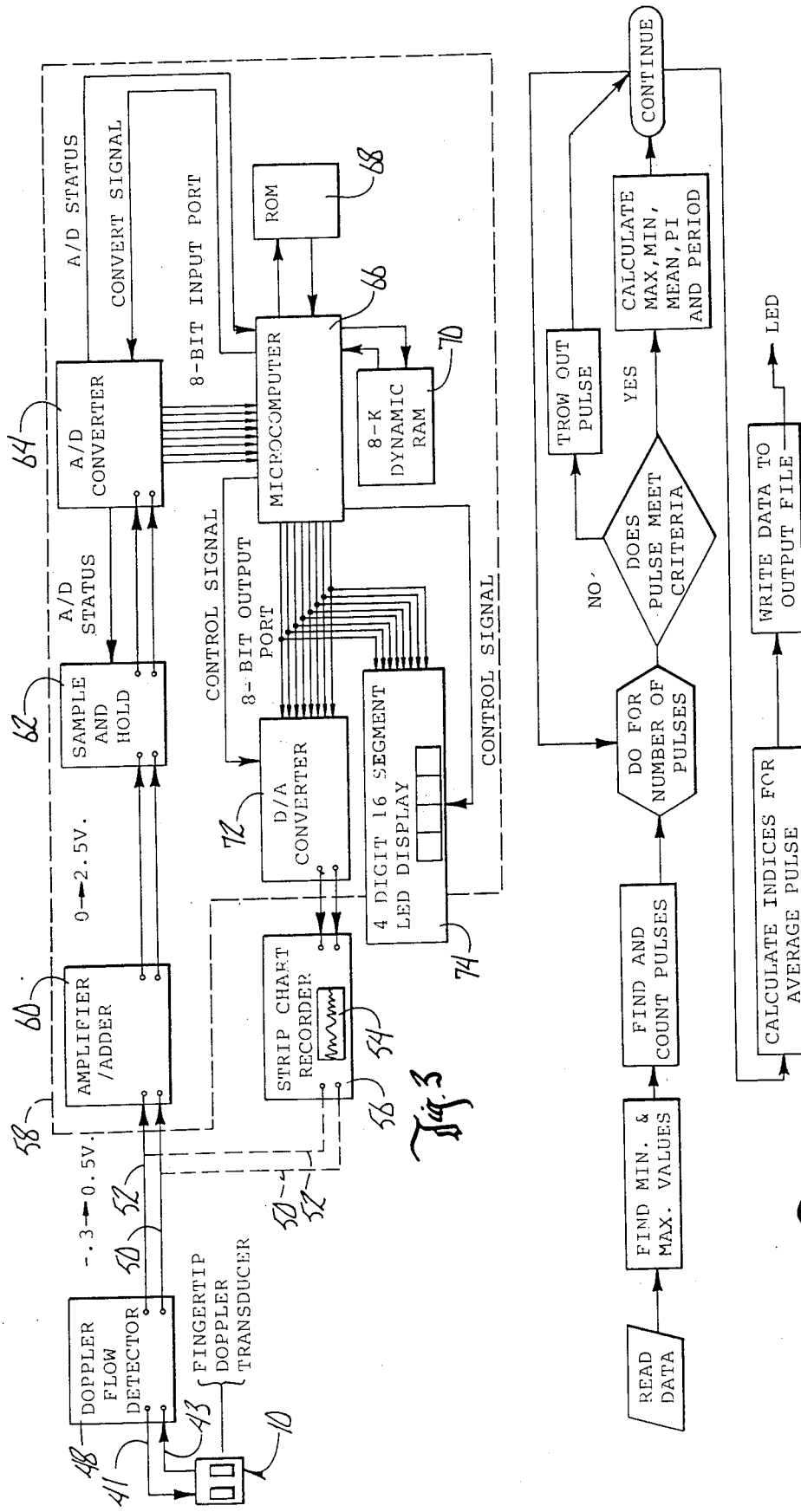

METHOD AND MEANS FOR DETECTING PREGNANCY IN DOMESTIC FARM ANIMAL

BACKGROUND OF THE INVENTION

The present invention relates to a method and means for detecting pregnancy in domestic farm animal species.

An important factor in efficient livestock management is concerned with maximizing conception rates in the livestock herd. For example, in the beef and dairy cattle industries, a desirable goal is a 12 month calving interval for each cow in the herd. The gestation period for a cow is about 283 days, and it is therefore important to have a pregnancy test which provides early diagnosis of pregnancy in the cow.

Presently there is no practical pregnancy test for cows which the livestock producer can routinely use to detect pregnancy in less than 30 days of gestation. Although most cows that fail to conceive will return to estrus in about 21 days after breeding, there is a small percentage that do not. While relatively small in number, this latter group is important to the livestock producer for obtaining the maximum efficiency in breeding. Non-pregnant cows need to be discovered as early as possible so they can be rebred in the next estrus period.

Present methods for pregnancy detection include such methods as an assay of milk progesterone. This test is based upon milk samples taken 21 to 24 days after breeding. However, this test must be conducted in a laboratory using highly sophisticated and expensive equipment. In addition, a significant number of non-pregnant cows are diagnosed as pregnant by this test, which reduces its value.

Another common technique for detecting pregnancy is rectal palpation, which appears to be the only practical means available to livestock producers. Through rectal palpation, it is possible to detect changes in the uterus associated with pregnancy, as early as 35 to 40 days postbreeding. Also, it is possible to palpate the middle uterine arteries to detect increased blood flow to the uterus associated with pregnancy, but not until the third or fourth month of pregnancy.

Therefore, a primary object of the present invention is the provision of a practical pregnancy test for domestic animals which the livestock producer can routinely use to detect pregnancy at an early period of gestation.

A further object of the present invention is the provision of a method and means for detecting pregnancy which is inexpensive and accurate.

A further object of the present invention is the provision of a method and means for detecting pregnancy which can be conducted at the farm by farm personnel without requiring professionals, such as veterinarians, to perform the test.

A further object of the present invention is the provision of a method and means for detecting pregnancy in cows as early as 14 to 18 days after breeding.

A further object of the present invention is the provision of a method and means for detecting pregnancy which may be used in domestic livestock other than cattle.

A further object of the present invention is the provision of a method and means for detecting pregnancy which relies upon the increased blood flow in the uterine artery of the animal.

A further object of the present invention is the provision of a method and means which are economical to manufacture and use and which are efficient in operation.

SUMMARY OF THE INVENTION

The technique of the present invention for early pregnancy diagnosis is based upon four concepts: the first of these concepts is that the blood flow through the middle uterine arteries supplying the uterine horn in which the fetus is developing is significantly increased over the blood flow through the opposite (contralateral) uterine artery as early as fourteen days after breeding.

The second concept is that the blood flow through the uterine arteries can be estimated by using ultrasonic crystals placed against the arteries during rectal palpation.

The third concept is that the differences in blood flow patterns between pregnant and non-pregnant cows can be quantified through an analysis of the shape of the flow waveforms.

The fourth concept is that an ultrasonic device can be designed and packaged into a simple relatively inexpensive unit that would be suitable for use at the farm by farm personnel.

The present invention utilizes a small receptacle that is adapted to fit over the human finger. On the receptacle is a transducer which is adapted to transmit an ultrasonic signal and to receive an ultrasonic echo signal in response thereto. The ultrasonic echo signal is received by the transducer and is converted to an electrical signal which is transmitted through an electrical lead to a Doppler flow detector. The Doppler flow detector converts the signal into a waveform which can be displayed on a strip chart recorder.

As an alternate to the use of the strip chart recorder, the present invention contemplates the use of a computer which takes the signal from the Doppler flow detector and converts it into a digital readout which provides an indication of the velocity of blood flow in the uterine artery.

The majority of the blood to the right and left uterine horns of cows is supplied through the right and left middle uterine arteries, respectively. The pattern of blood flow to both uterine horns of cows during the first thirty days of pregnancy is illustrated by FIG. 6 of the drawings. Between days 14 and 18 of pregnancy, blood flow through the uterine artery supplying the gravid horn is shown to increase substantially, whereas blood flow through the contralateral uterine artery is shown to remain relatively constant. At about day 25, the flow to the gravid horn again increases markedly and remains high during the course of pregnancy. From this, it has been determined that blood flow measurements obtained during early pregnancy can provide an indication of pregnancy.

The present invention contemplates the use of an ultrasonic device to estimate blood flow in the uterine artery. The device is based upon the Doppler effect in which there is a frequency shift that sound waves undergo when the distance between a sound generator (transmitter) and corresponding receiver is changing. Doppler flowmeters essentially consist of one or two small piezoelectric crystals. In a two crystal device, one crystal acts as a transmitter and sends out sound waves at ultrasonic frequencies. When these waves interact with the moving reflecting surface such as the red blood cell in an artery, the wave is reflected at a slightly different frequency which can be sensed with the second crystal (receiver). In a single crystal device, the single crystal acts both as a transmitter and a receiver. The basic formula for the frequency in this application is:

$$\Delta F = \frac{2fV\cos\phi}{C}$$

where $\Delta F$ is the difference between the emitted and received frequency, f is the frequency of the transmitter, V the velocity of the moving reflector, $\phi$ the angle between the ultrasonic beam and the direction of flow, and C is the velocity of sound in tissue. In a given application, all quantities except $\Delta F$ and V are fixed so that V is directly proportional to $\Delta F$.

In the piezoelectric device of the present invention, the shifted frequency is converted into a voltage which is transmitted to a conventional ultrasonic flowmeter capable of having an output voltage which is proportional to the velocity in the artery. Since the ultrasonic beam transverses the entire uterine artery, reflections from many blood cells are received so that the shifted frequency is really a mean value and the velocity measured is an approximation of the cross-sectional average velocity of the blood flow within the artery.

The present invention utilizes a receptacle which will fit over a human finger. On the receptacle is a transducer which may be either a single crystal or a double crystal transducer. In order to use the device, the operator locates the uterine artery by means of rectal palpation. Once the uterine artery is located through the rectal wall, the operator places the transducer over the uterine artery so that the ultrasonic transmitted signal will be directed toward the artery. The device receives the echo from the artery and transmits this echo through electrical leads to a Doppler flow detector which produces an electrical signal that is proportional to the velocity of the blood in the artery.

The output signal from the flow detector can be connected directly to a strip chart recorder which will produce a paper graph of the output signal. A typical graph is shown in FIGS. 5A and 5B.

In one modification of the present invention, a computer is connected to the Doppler flow detector and the computer is programmed to analyze the information and produce a digital readout indicating an index that is a measure of the velocity of the blood flow within the artery. Since the recording of the regular pulsatility of the blood flow through the artery is sometimes interrupted by uncontrolled contractions of the rectal wall or movements of the cow, these atypical recordings need to be screened out in order to properly analyze the velocity of the blood within the artery. The computer is programmed to delete the pulse cycles which are atypical so that a more accurate reading of the blood flow can be obtained.

In order to use the present invention, the operator need merely place the crystal on the uterine artery by means of rectal palpation. If the Doppler flow detector is connected to a strip chart recorder, the velocity of the blood flow will be indicated in a waveform on the strip chart which is produced by the strip chart recorder. Two readings are typically taken, one from each of the two uterine arteries. This will provide a means for comparison, with the nonpregnant uterine horn indicating one blood flow velocity and with the pregnant uterine horn indicating a different and higher blood flow velocity. Another method for establishing comparison is to measure the blood flow velocity of the uterine artery at a time when the cow is known not to be pregnant. This record can then be compared with the velocity at the time that pregnancy is suspected.

BRIEF DESCRIPTION OF THE FIGURES OF THE DRAWINGS

FIG. 3 is a schematic diagram of the electrical hardware utilized to analyze the data from the present invention.

FIG. 4 is a flow diagram of the computer program which is utilized in the computer for analyzing the data received by the transducer of the present invention.

DETAILED DESCRIPTION OF THE PREFERRED EMBODIMENT

Figure 1:
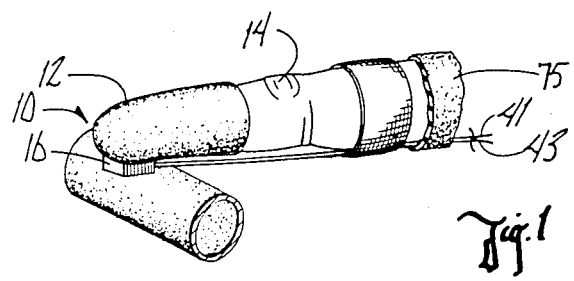
FIG. 1 is a pictorial view of the probe used in the present invention.

Referring to the drawings, the numeral 10 generally refers to the fingertip Doppler transducer device of the present invention. Device 10 includes a finger receptacle 12 preferably formed from an elastomeric material such as rubber so that it can fit frictionally over the end of a human finger designated by the numeral 14 in FIG. 1.

Figure 2:
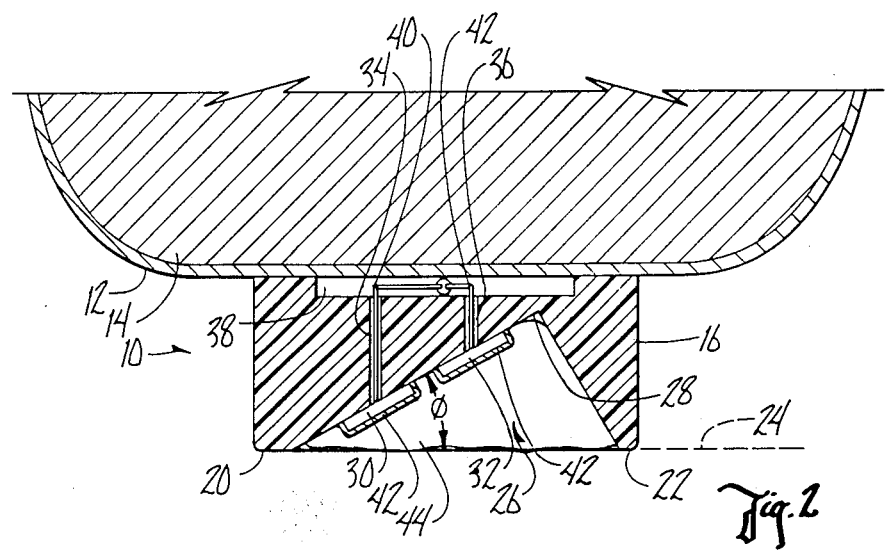
FIG. 2 is an enlarged sectional view of the probe and the transducer of the present invention.

Rigidly attached to the outer surface of receptacle 12 is a transducer housing 16 which is formed from a plastic material. Housing 16 is rectangular or circular in shape and is operatively attached to receptacle 12. Examples of methods of attachment may include sewing, using adhesive, or using other conventional fastening means. The bottom edges 20, 22 of transducer housing 16 define a plane designated by the numeral 24 in FIG. 2. A cavity 26 is formed within housing 16 and includes an inclined surface 28 which is at an angle $\phi$ with respect to the plane 24. The size of angle $\phi$ may vary without detracting from the invention. However, if surface 28 is parallel to the plane 24, it will be necessary to tilt the device when it is applied to the uterine artery so that the surface 28 will not be parallel to the direction of flow in the uterine artery. At the time of applying the transducer to the artery, it is important that the surface 28 be inclined with respect to the directional flow of the artery.

Mounted on surface 28 are a transmitting piezoelectric member 30 and a receiving piezoelectric member 32. While two separate piezoelectric members are shown, it is possible to utilize a single piezoelectric member which both transmits and receives ultrasonic waves. The preferred embodiment utilizes separate members for transmitting and receiving as shown in the drawings.

Extending upwardly through tranducer housing 16 are a pair of hollow bores 34, 36 which lead from a lead cavity 38 downwardly to the surfaces of piezoelectric members 30, 32. A pair of electrical leads 41, 43 extend from outside transducer housing 16 into cavity 38 where they are attached to leads 40, 42. Leads 40, 42 extend downwardly through bores 34, 36 respectively. The ends of leads 40, 42 are electrically connected by soldering or other means to piezoelectric members 30, 32, respectively.

Cavity 26 contains the piezoelectric members 30,32 which are attached to the surface 28. A thin coating of plastic or wax 42 covers the piezoelectric members 30, 32 to prevent damage during repeated usage. Prior to use the cavity is filled with an aqueous coupling gel 44 to provide a low resistance transmission path for the ultrasonic waves. After the Doppler transducer device is fitted to a finger a rubber glove 75 is then fitted over the entire hand.

Referring to FIG. 3, a schematic diagram is shown which includes the fingertip Doppler transducer 10. Leads 41, 43 are connected to a Doppler flow detector 48. While different Doppler flow detectors are commercially available, a preferred example of such a device is an ultrasonic Doppler flow detector Model 812, manufactured by Parks Medical Electronics, Inc. of Beaverton, Oreg. This device is capable of amplifying the signal from the transducer to produce an output signal which can be used to produce a visual display of the data transmitted to the Doppler flow detector from fingertip Doppler transducer 10. Doppler flow detector 48 can be connected directly to a conventional strip chart recorder 56 by means of electrical leads 50, 52 as indicated by phantom lines in FIG. 3. This will result in the strip chart recorder producing a graph chart 54 which can be analyzed to determine the velocity of blood flow within the artery upon which the transducer 10 is placed. various types of strip chart recorders 56 are commercially available and well known in the art.

An alternative modification of the present invention includes connecting the Doppler flow detector to a computer 58 by leads 50, 52 rather than connecting the Doppler flow detector 48 directly to the strip chart recorder 56.

Computer 58 includes the following components therein. An amplifier/adder 60 receives input directly from the Doppler flow detector 48. The signal from the flow detector 88 is proportional to the blood velocity and has a range of approximately −0.3 to +0.5 volts. The amplifier/adder 60 amplifies the signal and adds a DC voltage to give an output range of 0 to 2.5 volts. The signal is then sent to a sample and hold circuit 62 which samples the signal from the amplifier/adder and holds it steady for a period of approximately 10 microseconds.

Connected to the sample and hold circuit 62 is an A/D converter 64 which reads the input voltage from the sample and hold circuit 62 and converts this signal to an eight bit binary number between 0000 0000 and 1111 1111 (i.e., 0 through 255).

Connected to the A/D converter is a microcomputer which is preferably manufactured by Micromint Company of Vernon, Conn. under Model No. BCC 52. This computer runs a controlling program stored in a 16K read only memory (ROM) chip 68. Computer 66 controls the A/D converter 64, reads the input signal every ten milliseconds, and stores these data in a dynamic random access memory (RAM) 70. After 10–20 seconds of data are collected, the program analyzes the data and calculates a pulsatility index. A description of the program for producing this index, and the definition of the index will be provided hereafter.

As data are collected and stored by the computer, it is also sent simultaneously to a digital analog converter 72 which converts the data into an analog signal suitable for a strip chart recorder input which can be used by strip chart recorder 54. This makes possible the connection of the strip chart recorder directly to the D/A converter 72 so that a strip chart 54 will be produced (if desired) showing the analyzed data which has been handled by the computer 58.

The computer 58 also includes a four digit LED display 74. Display 74 may be a device manufactured by Litronix, of Cupertino, Calif., under the Model designation DL-1416. This is a four digit, 16 segment alpha numeric light emitting diode display with built-in memory, decoder, and driver. When the microcomputer has calculated the average pulsatility index of the standard, it sends a signal to the LED display 74 to display that number which can be observed visually. The computer is also capable of providing an estimate of the standard deviation of the data on the LED display 74.

Figure 7:
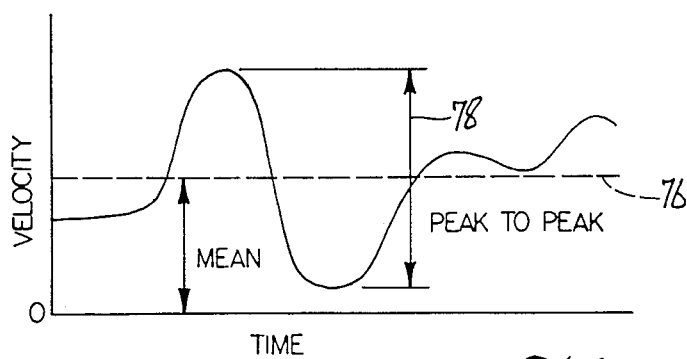
FIG. 7 is a graph showing a typical waveform of the blood flow velocity within the uterine artery with respect to time.

FIG. 4 is a flow chart showing the computer program which is stored in the read only memory chip 68. This program is used to analyze the waveform of the signal received from the fingertip Doppler transducer. A typical waveform is shown in FIG. 7. Due to the pulse of the animal, the velocity will vary with time in a waveform. The line 76 in FIG. 7 refers to the mean velocity of the blood flow measured. A peak to peak velocity is represented by the arrow 78. These two values are used to calculate a pulsatility- index which is represented by the following formula:

$$\text{Pulsatility index} = \frac{\text{peak to peak velocity}}{\text{mean velocity}}$$

This formula will give a pulsatility index which is inversely proportional to the velocity. That is, as the velocity of the blood flow increases, the pulsatility index will reduce in value. A low pulsatility index indicates a high blood flow velocity, and a high pulsatility index indicates a low blood flow velocity. Since the pulsatility index is the ratio of two velocities its value is independent of the angle between the ultrasonic beam and the direction of flow. The pulsatility index is indicated on the four digit display of the LED 74. As shown in FIG. 4, the computer program causes the microcomputer to first read the data from A/D converter 64. Next, the minimum and maximum values of the wave form are calculated. The number of pulses are then identified and counted. Then the number of pulses are analyzed against various criteria so as to identify pulses which are atypical and so as to produce a substantially homogeneous collection of pulses. The pulses which are atypical are deleted by the computer program.

The program then calculates a quantity proportonal to the maximum velocity, the minimum velocity and the mean, and uses these values to calculate the pulsatility index. The period of time for each cycle within the data is also calculated.

The program then causes the computer to calculate an average indice for the various pulses which are included within the data. After the average pulsatility index has been calculated, the program causes the computer to send the data to the light emitting diode 74, where the average pulsatility index is displayed. The data are also sent to the D/A converter 72 which can be connected to the strip chart recorder 56 so that a graphic display of the data which has been modified by the computer program can be displayed on graph chart 54.

Figure 5A:
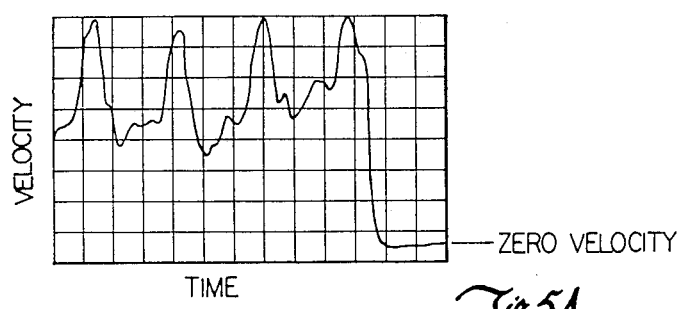
FIGS. 5A and 5B are graphs showing the comparative blood flow velocity in a pregnant and non-pregnant uterine horn, respectively.
Figure 5B:
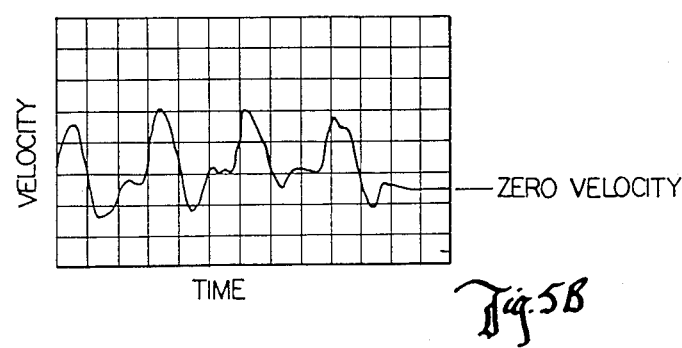

FIGS. 5A and 5B show the comparative data produced from a measurement taken in the left uterine artery of a cow (FIG. 5A), and the right uterine artery of the same cow (FIG. 5B). The graph in FIG. 5B shows the velocity in a non-impregnated horn of the cow, and the graph shown in FIG. 5A shows a typical reading of a uterine horn which has a developing embryo therein. A comparison of the two graphs shows that the pulsatility index for the pregnant horn of the uterus (FIG. 5A) is substantially lower in magnitude than the pulsatility index of the blood flow in the non-impregnated uterine horn thus indicating a higher mean velocity in the pregnant Horn. These measurements were taken approximately 18 days after breeding. They provide a clear and strong indication that the left uterine artery (FIG. 5A) has a developing embryo therein.

Figure 6:
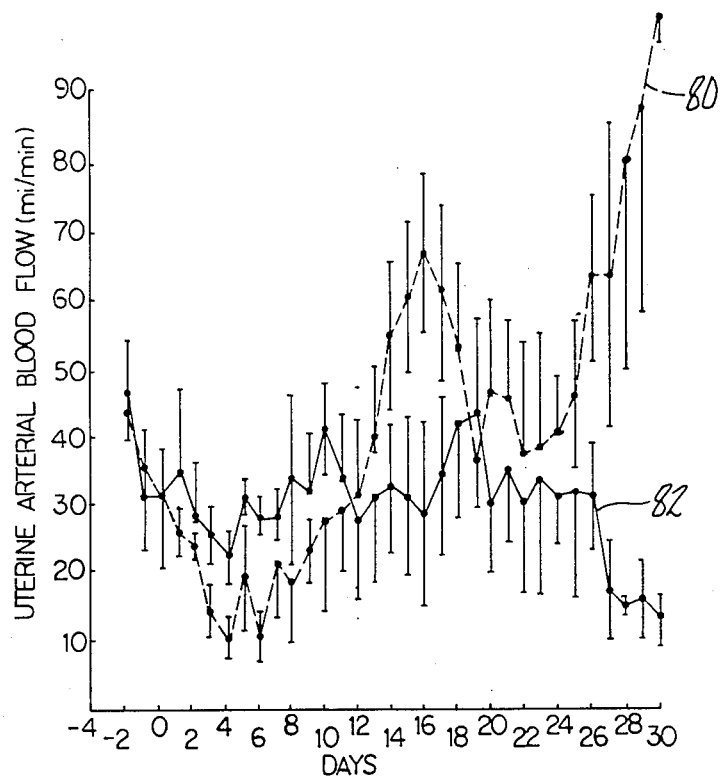
FIG. 6 is a graph showing the uterine arterial blood flow versus the first 30 days of pregnancy in a cow.

FIG. 6 shows a comparison of the mean blood flow (mean plus or minus the standard error of the means) in the uterine arteries of the two separate horns of three cows during the first 30 days of pregnancy. The numeral 80 shows the pattern of blood flow to the horn which contains a developing embryo therein, and the numeral 82 shows the blood flow through the uterine artery supplying the uterine horn which is not impregnated. The vertical lines which transverse lines 80, 82 represent the standard error of the mean, whereas the lines 80, 82 represent the mean flood flow at each measurement. As can be seen from FIG. 6, from the 14th to the 18th day there is a marked increase in the blood flow in the uterine artery of the horn which has a developing embryo therein. This blood flow increases again by day 24 and is substantially greater than that in the nongravid horn by approximately the 30th day of pregnancy.

During the first 30 days of pregnancy, it is very difficult for a layman to detect the pregnancy of the cow without the use of professional help or extremely expensive equipment. However, with the present invention, it is possible to use rectal palpation to insert the transducer of the present invention and to place the transducer in contact with the uterine artery to provide a pulsatility index which can be used to indicate changes in flow.

Thus, the present invention provides a means by which to detect pregnancy as early as the 14th to 18th day of pregnancy.

Use of this device allows pregnancy to be detected prior to the 30th day of pregnancy and therefore the present invention provides a substantial improvement over the currently used methods for detecting pregnancy.

The device of the present invention can be manufactured and made available to the stock breeder in relatively inexpensive form. Furthermore, it can be operated by a nonprofessional person such as the stock breeder, and does not necessarily require a veterinarian or other professional person. With training the operator can learn to locate the uterine artery by rectal palpation and to take the readings which have been described above. He need merely compare the pulsatility index displayed on the LED display 74 to determine the pregnancy. A comparison can be made between the two uterine arteries of the cow, or in the alternative, the breeder can compare the reading taken from the cow with an earlier reading taken at a time when it was known that the cow was not pregnant. In either case, an elevated blood flow velocity (represented by a reduced pulsatility index), will indicate pregnancy.

The device can be manufactured in a small compact case which can be easily transported to the feed lot or location of the cow.

The present device, while shown for use with cows, can also be used for other domestic livestock species. For example, the device can be used to detect changes in blood flow in the middle uterine artery for pigs, horses, or other livestock. The particular times for detection will vary with each specie of animal, depending upon the gestation period for that animal. For example with pigs, the detection can be made as early as 13 days after breeding.

Thus, the device accomplishes at least all of its stated objectives.

What is claimed is:

1. A method for detecting pregnancy in an animal having first and second uterine horns and first and second uterine arteries within said first and second uterine horns, respectively said method comprising:

taking a first measurement indicating the velocity of blood flow within said first uterine artery taking a second measurement of the velocity of blood flow within said second uterine artery;

comparing said first and second measurements whereby an elevation of one of said measurements substantially above the other of said measurements indicates pregnancy in the one of said uterine horns associated with said one elevated measurement.

2. A method according to claim 1 wherein said taking of said first and second measurements is accomplished by placing a transducer means in contact with said first and second uterine arteries, respectively, transmitting an ultrasonic transmitted signal from said transducer means into said first and second arteries, respectively, using said transducer means to receive an echo ultrasonic signal resulting from said transmitted signal, converting said ultrasonic echo signal to an electrical echo signal, and carrying said electronic echo signal to analyzing means for analyzing said electronic echo signal.

3. A method for detecting pregnancy in an animal comprising:

taking a first measurement indicating the velocity of blood flow within the uterine artery of said animal at a time when said animal is known not to be pregnant;

taking a second measurement indicating the velocity of blood flow within said uterine artery of said animal at a time when said animal is suspected of being pregnant, but before an embryo is readily detectable by manual palpation;

comparing said first and second measurements whereby pregnancy will be indicated by said second measurement being substantially greater than said first measurement.

4. A method according to claim 3 wherein said taking of said first and second measurements is accomplished by placing a transducer means in contact with said uterine artery, transmitting an ultrasonic transmitted signal from said transducer means into said uterine artery, using said transducer means to receive an ultrasonic echo signal resulting from said transmitted signal and to convert said ultrasonic echo signal into an electric echo signal, and carrying said electronic echo signal to analyzing means for analyzing said electronic signal.

* * * * *